United States Patent [19]

Kobayashi

[11] Patent Number: 5,153,125
[45] Date of Patent: Oct. 6, 1992

[54] PROCESS FOR PRODUCING LYSOPHOSPHOLIPIDS-CONTAINING PHOSPHOLIPIDS WITH REDUCED NEUTRAL LIPID CONTENT

[75] Inventor: Hideaki Kobayashi, Fuchu, Japan

[73] Assignee: Kewpie Kabushiki Kaisha, Tokyo, Japan

[21] Appl. No.: 78,686

[22] Filed: Jul. 28, 1987

[30] Foreign Application Priority Data

Jul. 28, 1986 [JP] Japan .................. 61-177142

[51] Int. Cl.⁵ .............. C12P 13/00; C12P 13/02; C12P 9/00
[52] U.S. Cl. .................... 435/128; 435/131; 554/79; 554/82; 554/83
[58] Field of Search .............. 435/128, 131; 260/403

[56] References Cited

U.S. PATENT DOCUMENTS 3,505,074  4/1970  Pardun .................. 260/403
3,652,397  3/1972  Pardun .................. 435/131

OTHER PUBLICATIONS

Perry, Chemical Engineer's Handbook, 5th Ed. (1973), 15-2.

Primary Examiner—Carolyn Elmore
Attorney, Agent, or Firm—Oblon, Spivak, McClelland, Maier & Neustadt

[57] ABSTRACT

Lysophospholipids-containing phospholipids with reduced neutral lipids content can be produced by a process which comprises subjecting neutral lipids- and lysophospholipids-containing phospholipids to treatment with acetone in the presence of an acid. In accordance with the present invention, it is possible to produce on a commercial scale by a simple procedure lysophospholipids-containing phospholipids wherein the neutral lipids content is reduced to 10% by weight or less of the total lipids content.

5 Claims, No Drawings

PROCESS FOR PRODUCING LYSOPHOSPHOLIPIDS-CONTAINING PHOSPHOLIPIDS WITH REDUCED NEUTRAL LIPID CONTENT

BACKGROND OF THE INVENTION

The present invention relates to a novel process for producing lysophospholipids-containing phospholipids with reduced neutral lipids content.

The lysophospholipid is obtained by the removal of one fatty acid unit per molecule from a phospholipid and the introduction of a hydroxyl group in place thereof and thus is more highly hydrophilic than the phospholipid. For this reason, lysophospholipids-containing phospholipids not only have good emulsifying capability inherent in the phospholipids but are said to be capable of forming spherical micelles in an aqueous solution to solubilize water-insoluble substances in transparent state unlike phospholipids containing no or substantially no lysophospholipids, and are therefore expected to be applicable as a solubilizer in the fields of food, cosmetics and drugs. Ordinarily, the lysophospholipids-containing phospholipids obtained by subjecting phospholipids derived from organisms to an enzymatic action contain a considerable quantity of neutral lipids. In the case where the content of the neutral lipids exceeds 10% of the total lipids content, it has been found difficult to obtain the solubilizing effect mentioned above. For this reason, various attempts have so far been made to reduce the neutral lipids content in lysophospholipids-containing phospholipids.

As a method for removal of neutral lipids from neutral lipids-containing phospholipids to obtain purified phospholipids, the acetone precipitation method has heretofore been known in the art (for example, The Japan Chemical Society (ed.), "Shin Jikken Kagaku Koza (A New Series of Lectures on Experimental Chemistry) 20, Seibutsu-Kagaku (Biochemistry) (I)", pp. 418-419 (1978)). In accordance with this method, neutral lipids are separated as acetone solubles from phospholipids as acetone insolubles. Commercially available purified soybean phospholipid or purified egg yolk phospholipid is ordinarily obtained by this method, and even phospholipids of a grade as high as 98% are produced on a commercial scale. Also is known an improved method wherein an inorganic salt such as magnesium chloride is added during the treatment with acetone to improve the insolubility of phospholipids in acetone.

When neutral lipids- and lysophospholipids-containing phospholipids are subjected to the above described acetone treatment, even when it is repeated several times, however, the neutral lipids content therein can be reduced at best to about 15% as will be apparent from the test results set forth hereinlater. Such lysophospholipids-containing phospholipids are not only inapplicable as solubilizers but also are accompanied by the problem of reduced stability such that they become susceptible to oxidation and like changes since the residual neutral lipids contain free unsaturated fatty acids such as oleic acid, linolic acid, linolenic acid, arachidonic acid and docosahexaenoic acid which were produced when the phospholipids were subjected to an enzymatic action (for example, to the action of phospholipase $A_2$), thus forming peroxidated lipids which give out an unpleasant odor.

As another method for removal of neutral lipids from lysophospholipids-containing substances, solvent fractionation comprising the sequential steps of methanol extraction-chloroform/water distribution-80% methanol/hexane distribution ethanol extraction-isopropanol extraction and the like (as is disclosed, for example, in Japanese Patent Laid-Open Pub. No. 315/1980) or the solvent fractionation in combination with column chromatography using silica gel and the like has been known heretofore. Admittedly, these methods have been found effective to some extent from the point of view of the removal of neutral lipids but, on the other hand, are accompanied by various problems such as that they involve complicated manipulation and are also time-consuming and very expensive.

Under such circumstances, an object of the present invention is to provide a process whereby lysophospholipids-containing phospholipids with reduced neutral lipids content, more specifically with a neutral lipids content of 10% or less of the total lipids content, can be produced on a commercial scale by a simple procedure.

SUMMARY OF THE INVENTION

As a result of extensive research effort expended toward attaining the above object, I have found that, by carrying out treatment with acetone in the presence of an acid in the acetone precipitation method which has hitherto been acknowledged as a typical method for obtaining purified phospholipids, neutral lipids can be removed very effectively from neutral lipids- and lysophospholipids-containing phospholipids. On the basis of this finding, I have arrived at the present invention.

More specifically, the present invention provides a process for producing lysophospholipids-containing phospholipids with reduced neutral lipids content which comprises subjecting neutral lipids- and lysophospholipids-containing phospholipids to treatment with acetone in the presence of an acid.

DETAILED DESCRIPTION OF THE INVENTION

I. Neutral lipids- and Lysophospholipids-Containing Phospholipids

I-1 Definition:

The starting neutral lipids- and lysophospholipids-containing phospholipids to which the process of the present invention is applicable are lysophospholipids-containing phospholipids obtained by subjecting phospholipids derived from organisms to an enzymatic action and containing more than 10% of the total lipids content of neutral lipids, the rate of the lysophospholipids in the total phospholipids being not less than 20%. The rate of the lysophospholipids content herein is critical because, in the case of phyospholipids containing less than 20% of lysophospholipids, the content of neutral lipids can be reduced to 10% or less of the total lipids content by the conventional acetone precipitation method.

Specific examples of such starting phospholipids are those obtained by subjecting glycerophospholipids or substances comprising the same as one primary ingredient to treatment with phospholipase A2 or to alkali hydrolysis to convert 20 to 100% of the phospholipids in the starting material into lysophospholipids. These phospholipids generally contain lysophosphatidylcholine (LPC), lysophosphatidylethanolamine (LPE), lysophosphatidic acid (LPA), lysophosphatidylinositol (LPI) and lysophosphatidylserine (LPS) as the lysophospholipids and further contain triglyceride, diglyceride, monoglyceride, fatty acids and sterols as the neutral lipids. More specific examples of the starting phospholipids are the thus obtained crude lysophospholipids comprising 70% of neutral lipids and 30% of phospholipids (the lysophospholipids content being 28%) and crude lysophospholipids-containing substances comprising 46% of lipids (the neutral lipids content being 28% and the phospholipids content being 72% (including 51% of lysophospholipids)), 52% of protein and 2% of water. All percentages set forth herein are % by weight unless otherwise indicated.

I-2 Preparation:

A typical example of the process for preparing neutral lipids- and lysophospholipids-containing phospholipids as mentioned above will be described hereinafter.

Neutral lipids-containing phospholipids derived from organisms, such as animal or plant tissue or microorganism cells containing a large quantity of phospholipids, for example, egg yolk, bovine brain, porcine brain, soybean, rapeseed, chlorella cells, and mould cells (including Cunninghamella microoganism cells), and crude phospholipid extracts obtained from these animal or plant tissue or microorganism cells, for example, commercially available soybean phospholipid (ordinarily containing 60% or more phospholipids) and commercially available egg yolk phospholipid (ordinarily containing 30% or more phospholipids), are preferably crushed or liquefied, when used, in order to ensure an effective enzymatic action and then subjected to an action of a phospholipase $A_2$ preparation or an enzyme preparation containing phospholipase $A_2$ to convert the phospholipids therein into lysophospholipids.

Examples of the phospholipase $A_2$ preparation or the enzyme preparation containing phospholipase $A_2$ for use herein are mixtures of enzymes extracted from animal pancreas, such as pancreatin, pancreatin subjected to a heat treatment to deactivate protease and lipase for enrichment with phospholipase $A_2$ (reference: Japanese Patent Laid-Open Pub. No. 88040/1984), a purified phospholipase $A_2$ preparation derived from animal pancreas, and a phospholipase $A_z$ preparation derived from snake venom or bee toxin, commercially available preparations of equivalent character being advantageously used.

The enzyme reaction using the above enzyme preparations may be carried out in accordance with a conventional method under the conditions not limitedly determined in the present invention but suitably selected so that 20 to 100% of the phospholipids can be converted into lysophospholipids in the practice of the reaction. In order to increase the conversion into lysophospholipids, the enzymatic hydrolysis should be conducted over a long period of time.

Ordinarily, the product obtained by this enzyme reaction is then subjected to the step of extracting the lysophospholipids therefrom with a polar solvent. I have further found that, if the reaction product is dried to reduce the water content thereof to 10% or less prior to the extraction, the enzyme used will not transfer into the extract obtained in the subsequent step of solvent extraction whereby neutral lipids- and lysophospholipids-containing phospholipids with substantially no residual enzyme activity of phospholipase $A_2$ can be obtained.

The means for drying the reaction product is not limited, and any conventional drying means can be utilized although the temperature of the reaction product should not exceed 80° C. during drying so that it will not undergo denaturation due to excessive heat. If a spray drying or freeze-drying means is adopted, the temperature of the reaction product per se will be maintained at approximately 60° C. at the highest, and thus the protein contained therein will undergo no denaturation or substantially no denaturation due to heat, resulting in high extraction efficiency of lysophospholipids in the subsequent step of solvent extraction. Ordinarily, the reaction product dried to reach a water content of 10% or less is in powder form.

The powdery product thus obtained is then subjected to extraction with a polar solvent to extract lysophospholipids therefrom. The polar solvent used herein is not limited, and ethanol, methanol, a chloroform-methanol mixture or ethyl acetate can be employed, ethanol and methanol being especially preferred. The mode of solvent extraction is not limited, either, and may be carried out in accordance with a conventional method. By, for example, distilling the solvent off from the resulting extract under reduced pressure, lysophospholipids-containing phospholipids having substantially no residual enzyme activity can be obtained. Typically, the lysophospholipids-containing phospholipids further containing more than 10% of the total lipids content of neutral lipids thus obtained are the starting neutral lipids- and lysophospholipids-containing phospholipids for use in the process of the present invention.

The term "having substantially no residual enzyme activity" as used herein is intended to mean that the residual phospholipase $A_2$ activity is not higher than 0.1 IU per g of the neutral lipids- and lysophospholipids-containing phospholipids thus obtained, 1 IU (1 international unit) indicating the enzyme activity level sufficient to release 1 $\mu$mol of a fatty acid per minute from the substrate. If the starting material used in the process of the present invention has a residual enzyme activity exceeding 0.1 IU/g. the end product obtained, for example, when blended into another food product, would contribute to deterioration of the product since an enzyme reaction proceeds during storage to form a free fatty acid.

II. Treatment with Acetone

In accordance with the process of the present invention, neutral lipids- and lysophospholipids-containing phospholipids as described above are subjected to treatment with acetone in the presence of an acid whereby the content of the neutral lipids therein can be reduced.

The acetone treatment in the process of the present invention conforms to the conventional acetone precipitation method except that this treatment is carried out in the presence of an acid. As the acid, any of inorganic acids such as hydrochloric acid, sulfuric acid and nitric acid and organic acids such as acetic acid and citric acid may be used. The quantity of the acid added may vary depending upon the starting crude lysophospholipids (including a crude lysophospholipids-containing substance) or the acid selected and hence is difficult to determine. In general, however, quantities of 0.05% or more of the crude lysophospholipids may be sufficient. Below 0.05%, it is difficult to reduce the content of the neutral lipids in the starting material to 10% or less. If an excessive quantity of an acid is used, on the contrary, the acid cannot be removed easily although the neutral lipids can be removed effectively.

Since the acetone treatment according to the present invention is carried out in the presence of an acid as has been mentioned hereinabove, it is preferable to use a container and the like resistant to corrosion with an acid in the practice of the treatment.

In accordance with the process of this invention, the neutral lipids content in the starting material can be reduced very effectively, whereby it is possible to produce phospholipids with relatively increased lysophospholipids content, for example, purified lysophospholipids-containing phospholipids comprising 10% or less of neutral lipids and 90% or more of phospholipids (the lysophospholipids content being not less than 20%), and more specifically, a purified product comprising 5.2% of neutral lipids and 94.8% of phospholipids (the lysophospholipids content being 62.0%) or comprising 0.5% neutral lipids and 99.5% of phospholipids (the lysophospholipids content being 98.2%).

III. Meritorious Effects of the Process of the Present Invention

The phospholipids obtained by the process of the present invention, having reduced neutral lipids content and relatively increased lysophospholipids content, can be utilized not limitedly as emulsifiers or suspending agents likewise ordinary phospholipids but also as good solubilizers, and hence can be expected to have a wider application in numerous fields, inter alia, in solubilizing oil-soluble vitamins or flavors in various beverages in the field of food, solubilizing perfumes in lotions in the field of cosmetics, and further solubilizing various drugs in injections in the field of drugs. Furthermore, in the light of the latest researches for development of lysophospholipids as carcinostatic agents in the field of drugs, the product of the present invention can also be expected to be applicable as a starting material for physiologically active phospholipids, for example, for such carcinostatic agents.

The present invention has ensured production of lysophospholipids-containing phospholipids with reduced neutral lipids content having the above stated advantages simply by introducing into the conventional acetone precipitation method the improvement which comprises carrying out this method in the presence of an acid, providing a process whereby the desired substance can be produced on a commercial scale by an extremely simple procedure unlike the conventional process such as solvent fractionation comprising sequential extraction steps or the solvent fractionation in combination with column chromatography using silica gel and the like which involves complicated manipulation and is also time-consuming and very expensive.

EXAMPLES

The present invention will now be described more fully in greater detail with reference to specific examples of practice.

EXAMPLE I

To 100 kg of egg yolk was added a solution of 5 kg of pancreatin supplied by Wako Junyaku K.K., Japan (having phospholipase $A_2$ activity) dissolved in 10 kg of pure water, and the mixture was subjected to a reaction at 35° to 45° C. for 6 hours with stirring while the pH thereof was maintained at 7.0 to 8.0 with an aqueous solution of sodium hydroxide. Through this enzyme reaction, phosphatidylcholine (PC) which is the primary constituent of the egg yolk phospholipids is converted into LPC and phosphatidylethanolamine (PE) is converted into LPE.

The egg yolk reaction solution was then freeze-dried to obtain 47.2 kg of a dried product having a water content of 4.9%. To this dried product was added 400 liters of methanol, and extraction was carried out at 30° to 40° C. for 30 minutes with stirring, followed by filtration. The extract thus obtained was concentrated in vacuo (the temperature of the extract being maintained at 30° C. or lower) to obtain 21.8 kg of yellow paste-like crude egg yolk lysophospholipids.

The composition of the lipids was analyzed by means of IATROSCAN TH-10 (TLC/FID) (supplied by Yatron K.K., Japan) under the following measurement conditions, whereupon the crude lysophospholipids were found to comprise 74.1% of neutral lipids (essentially comprising triglyceride, fatty acids and cholesterol) and 25.9% of phospholipids (containing 24.2% of LPC and LPE). The residual enzyme activity of this crude product was found to be not higher than 0.1 IU/g.

Measurement Conditions

Rod: Chromarod S-II (silica gel)
Developing Solvent: Chloroform:Methanol:Water = 80:35:3 (v/v/v)
Developing Distance: 10 cm

Measurement 500 mg of each test sample was dissolved in a 2:1 (v/v) chloroform-methanol solution mixture, and 1 μl of the resulting solution was spotted on a rod. The sample solution was develped, air-dried and thereafter analyzed by means of IATROSCAN. The lipid composition was determined on the basis of the area ratio of the respective peaks.

Subsequently, to 1 kg each of the crude lysophospholipids obtained above were added 10 liters of acetone and then, as an acid, varying quantities of conc. hydrochloric acid or glacial acetic acid. The resulting mixture was stirred at 10° C. for 30 minutes, and the precipitate formed was filtered to obtain acetone insolubles. To each of these acetone insolubles was added 10 liters of acetone, and the mixture was again stirred and subjected to filtration under the same conditions to obtain acetone insolubles.

As controls, the above procedure was followed under the stated conditions except that the acid was not added, and the treatment with acetone was repeated three times and five times, respectively, to obtain acetone insolubles.

From all of the acetone insolubles thus obtained was removed the solvent under vacuum to obtain white powders. The yields of the respective powders were determined while the lipid compositions thereof were calculated on the basis of the peaks obtained through IATROSCAN TH-10 in accordance with the above measurement method. The results are summarized in TABLE 1 below.

TABLE 1

| Acetone treatment conditions | Acid not added | | Conc. hydrochloric acid | | | | Glacial acetic acid |
|---|---|---|---|---|---|---|---|
| | Treated with acetone 3 times | Treated with acetone 5 times | 0.05% | 0.20% | 0.70% | 1.00% | 0.70% |
| Yield | 22.0% | 20.2% | 20.2% | 19.8% | 19.1% | 18.5% | 19.7% |
| Lipid composition | | | | | | | |
| Neutral lipids content: | 14.5% | 14.0% | 8.9% | 3.9% | 1.8% | 0.5% | 6.2% |
| Total phospholipids content: | 85.5% | 86.0% | 91.1% | 96.1% | 98.2% | 99.5% | 93.8% |

Remarks: The quantity of the acid added is indicated in terms of the percentage relative to that of the crude lysophospholipids.

EXAMPLE 2

To 60 kg of commercially available soybean phospholipid (comprising 38% of neutral lipids and 62% of phospholipids) was added a solution of 30 g of a commercially available phospholipase $A_2$ preparation dissolved in 3 liters of pure water, and the resulting solution was subjected to a reaction at 55° C. for 24 hours with stirring while the pH thereof was maintained at 8.0 to 8.5 with an aqueous solution of calcium hydroxide. To the reaction solution were added 60 kg of pure water and 12 kg of dextrin powder as a vehicle. The resultant mixture was emulsified in a homogenizer and then subjected to spray drying (at an intake air temperature of 150° to 170° C. and an exhaust gas temperature of 50° to 75° C.) to obtain 68.4 kg of a powder having a water content of 3.6%.

The powder thus obtained was subjected to extraction in accordance with the Folch method (Yasuhiko Fujino, "Seibutsu-Kagaku Jikken-ho (Method of Biochemical Experiment) 9: Shishitsu Bunseki-ho Nyumon (Introduction to Lipid Analysis Procedures)", pp. 42–43) to obtain 57.5 kg of crude lysophospholipids.

The composition of the lipids was analyzed in accordance with the measurement method set forth in Example 1, whereupon the lipids were found to comprise 39.0% of neutral lipids (essentially comprising triglyceride, fatty acids and sterols) and 61.0% of phospholipids (containin9 22.5% of LPC, LPE, LPI and LPS). The residual enzyme activity of this crude product was found to be not higher than 0.1 IU/g.

Subsequently, 1 kg each of the crude lysophospholipids thus obtained were subjected to the same course of treatment with acetone as in the preceding Example 1. The results are set forth in TABLE 2 below.

moving neutral lipids improves as the quantity of the acid added increases.

EXAMPLE 3

To 5 kg. of the crude egg yolk lysophospholipids obtained in Example 1 was added 50 liters of acetone, and the mixture was gently stirred. To the resulting solution was added 25 ml of conc. hydrochloric acid, and the mixture was vigorously stirred at 10° C. for 30 minutes. The precipitate formed was filtered to obtain acetone insolubles to which was added 50 liters of acetone solely. The mixture was again stirred and subjected to filtration under the same conditions to obtain acetone insolubles. This procedure was repeated once more, and the solvent was removed in vacuo from the acetone insolubles obtained to yield 1.10 kg of purified egg yolk lysophospholipids in the form of a white powder.

The composition of the lipids was analyzed in accordance with the measurement method described in Example 1, whereupon the lipids were found to comprise 1.5% of neutral lipids (essentially comprising cholesterol) and 98.5% of phospholipids (containing 97.1% of LPC and LPE).

EXAMPLE 4

To 7 kg of the crude egg yolk lysophospholipids obtained in Example 1 was added 62 liters of acetone, and the mixture was gently stirred. To the resulting solution was added 19 ml of conc. hydrochloric acid, and the mixture was vigorously stirred at 10° C. for 20 minutes. The precipitate formed was filtered to obtain acetone insolubles to which were again added 62 liters of acetone and 19 ml of conc. hydrochloric acid. The mixture was stirred and subjected to filtration under the same conditions to obtain acetone insolubles. To the

TABLE 2

| Acetone treatment conditions | Acid not added | | Conc. hydrochloric acid | | | | Glacial acetic acid |
|---|---|---|---|---|---|---|---|
| | Treated with acetone 3 times | Treated with acetone 5 times | 0.05% | 0.20% | 0.70% | 1.00% | 0.70% |
| Yield | 57.8% | 55.3% | 54.8% | 53.1% | 52.7% | 51.2% | 53.2% |
| Lipid composition | | | | | | | |
| Neutral lipids content: | 10.5% | 10.2% | 5.6% | 2.8% | 1.9% | 0.3% | 2.5% |
| Total phospholipids content: | 89.5% | 89.8% | 94.4% | 97.2% | 98.1% | 99.7% | 97.5% |

It is apparent from the results obtained in Examples 1 and 2 above that, by carrying out the treatment with acetone in the conventional acetone precipitation method in the presence of an acid, even neutral lipids contained in lysophospholipids-containing phospholipids can be reduced very effectively, more specifically to 10% or less of the total lipids content. It is also apparent that the desired effects can be obtained irrespective of whether an inorganic acid or an organic acid is used therein. Furthermore, it is noted that the effect of reacetone insolubles thus obtained was further added 62 liters of acetone solely, and the mixture was subjected to the same procedure once more. The solvent was then removed in vacuo from the acetone insolubles obtained to yield 1.53 kg of purified egg yolk lysophospholipids in the form of a white powder.

The composition of the lipids was analyzed in accordance with the measurement method described in Example 1, whereupon the lipids were found to comprise 2.0% of neutral lipids (essentially comprising cholesterol) and 98.0% of phospholipids (containing 97.3% of LPC and LPE).

EXAMPLE 5

To 57.5 kg of crude soybean lysophospholipids obtained similarly as in Example 2 was added 500 liters of acetone, and the mixture was gently stirred. To the resulting solution was added 600 ml of glacial acetic acid, and the mixture was stirred at 10° C. for 30 minutes. The precipitate formed was filtered to obtain acetone insolubles to which was added 500 liters of acetone solely. The mixture was again stirred and subjected to filtration under the same conditions to obtain acetone insolubles. This procedure was repeated once more, and the solvent was removed in vacuo from the acetone insolubles obtained to obtain 29.5 kg of purified soybean lysophospholipids in the form of a pale yellow powder.

The composition of the lipids was analyzed in accordance with the measurement method set forth in Example 1, whereupon the lipids were found to comprise and 99.3% of phospholipids (containing 36.6% of LPC, LPE, LPI and LPS).

EXAMPLE 6

To 40 kg of egg yolk was added a solution of 40 g of a commercially available phospholipase $A_2$ preparation dissolved in 1 liter of pure water, and the resulting solution was subjected to a reaction at 40° to 50° C. for 5 hours with stirring while the pH thereof was maintained at 7.0 to 8.0 with an aqueous solution of sodium hydroxide.

To this egg yolk reaction solution was added 400 liters of acetone, and the mixture was stirred at 10° to 15° C. for 30 minutes. The precipitate formed was filtered to obtain 18.6 kg of a precipitate. To this precipitate were added 400 liters of acetone and 65 ml of conc. hydrochloric acid, and the mixture was stirred at 10° to 15° C. for 30 minutes. The precipitate formed was filtered, and the solvent was removed therefrom in vacuo to obtain 9.0 kg of acetone insolubles comprising proteins and phospholipids.

To the thus obtained acetone insolubles having a water content of 3.7% was added 90 liters of ethanol, and the phospholipids were extracted from the insolubles at 30° to 35° C. over a period of 30 minutes with stirring. The extract obtained by filtration was concentrated in vacuo to obtain 1.9 kg of a white powdery substance.

The lipid composition of the powdery substance was analyzed in accordance with the measurement method set forth in Example 1, whereupon this substance was found to comprise 0.6% of neutral lipids (essentially comprising cholesterol) and 99.4% of phospholipids (containing 95.1% of LPC and LPE). The residual enzyme activity of this substance was found to be 0.1 IU/g.

I claim:

1. A process for producing lysophospholipids-containing phospholipids with reduced neutral lipids content which comprises subjecting neutral lipids-containign phospholipids derived from organisms to the action of a phospholipase $A_2$ preparation or an enzyme preparation containing phospholipase $A_2$ to convert the phospholipids therein into lysophospholipids; drying the resultant phospholipids until the water content thereof is reduced to 10% or less; extracting the lysophospholipids therefrom with a polar solvent; distilling the polar solvent off from the extract to obtain neutral lipids- and lysophospholipids-containing phospholipids having substantially no residual enzyme activity; and then subjecting the phospholipds thus obtained containing more than 10% by weight neutral lipids to treatment with acetone in the presence of at least 0.05% by weight of the lysophospholipids of an added acid.

2. A process as claimed in claim 1, wherein the neutral lipids content is reduced to 10% by weight or less of the total lipids content.

3. A process as claimed in claim 1, wherein the drying is carried out by spray drying or freeze-drying.

4. A process as claimed in claim 1, wherein the acid is hydrocholoric acid, sulfuric acid, nitric acid, acetic acid or citric acid.

5. A process as claimed in claim 1, wherein the lysophospholipids content of the phospholipids subjected to treatment with acetone in the presence of the added acid is not less than 20% by weight.

* * * * *